United States Patent
Kamo (10) Patent No.: US 10,007,105 B2
(45) Date of Patent: Jun. 26, 2018

(54) OBJECTIVE OPTICAL SYSTEM FOR ENDOSCOPE

(71) Applicant: OLYMPUS CORPORATION, Hachioji-shi, Tokyo (JP)

(72) Inventor: Yuji Kamo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/585,658

(22) Filed: May 3, 2017

(65) Prior Publication Data

US 2017/0235123 A1 Aug. 17, 2017

Related U.S. Application Data

(63) Continuation of application No. PCT/JP2016/066668, filed on Jun. 3, 2016.

(30) Foreign Application Priority Data

Jun. 16, 2015 (JP) .................................. 2015-121162

(51) Int. Cl.
*G02B 9/60* (2006.01)
*G02B 23/24* (2006.01)
(Continued)

(52) U.S. Cl.
CPC ........ *G02B 23/243* (2013.01); *A61B 1/00163* (2013.01); *G02B 9/34* (2013.01); *G02B 9/60* (2013.01)

(58) Field of Classification Search
CPC ... G02B 9/60; G02B 9/62; G02B 9/64; G02B 13/0045; G02B 23/2407; G02B 23/243
(Continued)

(56) References Cited

U.S. PATENT DOCUMENTS 5,175,649 A * 12/1992 Uzawa ................. G02B 15/177
359/676
6,327,101 B1 * 12/2001 Miyano .................... G02B 9/34
359/642
(Continued)

FOREIGN PATENT DOCUMENTS

JP 2004061763 A 2/2004
JP 2009223183 A 10/2009
(Continued)

OTHER PUBLICATIONS

International Search Report (ISR) and Written Opinion dated Aug. 16, 2016 issued in International Application No. PCT/JP2016/066668.
(Continued)

*Primary Examiner* — Darryl J Collins
(74) *Attorney, Agent, or Firm* — Holtz, Holtz & Volek PC (57) ABSTRACT

An objective optical system for endoscope includes, in order from an object side: a first lens having a negative refractive power; a second meniscus lens having a positive refractive power with a convex surface thereof directed toward the object side; an aperture stop; a third lens having a biconvex shape, and a cemented lens having a positive refractive power as a whole, in which a fourth lens having a biconvex shape and a fifth lens having a negative refractive power are cemented.

8 Claims, 6 Drawing Sheets

(51) Int. Cl.
*A61B 1/00* (2006.01)
*G02B 9/34* (2006.01)

(58) Field of Classification Search
USPC ........ 359/708–714, 746, 749–753, 754–756, 359/761, 763, 770
See application file for complete search history.

(56) References Cited

U.S. PATENT DOCUMENTS

| | | | |
|---|---|---|---|
| 2008/0080061 A1* | 4/2008 | Miyano | G02B 23/243 359/661 |
| 2009/0237807 A1 | 9/2009 | Sasamoto | |
| 2011/0211267 A1 | 9/2011 | Takato | |
| 2012/0127598 A1* | 5/2012 | Katahira | G02B 9/34 359/770 |
| 2014/0268369 A1 | 9/2014 | Chen et al. | |
| 2015/0241664 A1* | 8/2015 | Wu | G02B 9/62 359/714 |

FOREIGN PATENT DOCUMENTS

| | | |
|---|---|---|
| KR | 100457967 B1 | 11/2004 |
| WO | 2010119640 A1 | 10/2010 |

OTHER PUBLICATIONS

International Preliminary Report on Patentability (IPRP) dated Dec. 28, 2017 issued in counterpart International Application No. PCT/JP2016/066668.

* cited by examiner

OBJECTIVE OPTICAL SYSTEM FOR ENDOSCOPE

CROSS-REFERENCE TO RELATED APPLICATION

The present application is a continuation application of PCT/JP2016/66668 filed on Jun. 3, 2016 which is based upon and claims the benefit of priority from Japanese Patent Application No. 2015-121162 filed on Jun. 16, 2015; the entire contents of which are incorporated herein by reference.

BACKGROUND OF THE INVENTION

Field of the Invention

The present invention relates to an objective optical system for endoscope, and particularly to an objective optical system for endoscope which can be used in an endoscope apparatus that is used in a medical field or an industrial field.

Description of the Related Art

An endoscope is an apparatus that has been used widely in the medical field and the industrial field. In the medical field in particular, images achieved by an endoscope inserted into an abdominal cavity have been used for diagnosis and treatment of a site observed.

In an optical system of an endoscope, by setting an appropriate F-number, it is possible to achieve a focused image from a near-point object up to a far-point object. Moreover, by making small a lens diameter and an overall optical length, is possible to arrange an endoscope having a small diameter, which does not cause pain while being inserted, and which is capable of turning in a small radius inside the body. In recent years, endoscopes with even superior image quality and further smaller size have been sought.

As an objective optical system for endoscope of a small size, there are objective optical systems proposed in Japanese Patent Application Laid-open Publication No. 2004-061763, Japanese Patent Application Laid-open Publication No. 2009-223183 and International Unexamined Patent Application Publication No. 10/119640.

SUMMARY OF THE INVENTION

The present invention provides the following means.

According to an aspect of the present invention, it is an objective optical system for endoscope, comprising in order from an object side:

a first lens having a negative refractive power;

a second meniscus lens having a positive refractive power with a convex surface thereof directed toward the object side;

an aperture stop;

a third lens having a biconvex shape, and a cemented lens having a positive refractive power as a whole, in which a fourth lens having a biconvex shape and a fifth lens having a negative refractive power are cemented, wherein the objective optical system for endoscope satisfies the following conditional expressions (1), (2), and (9)

$$-3 \leq f_1/Ih \leq -1.2 \quad (1)$$

$$0.25 \leq L_{3\_5}/L \leq 0.7 \quad (2)$$

$$0.2 \leq r_2/r_3 \leq 0.8 \quad (9)$$

where, $f_1$ denotes a focal length of the first lens;

Ih denotes the maximum image height of the objective optical system for endoscope;

$L_{3\_5}$ denotes a distance along an optical axis from a surface on the object side of the third lens up to a surface on an image side of the fifth lens, L denotes a distance along the optical axis from a surface on the object side of the first lens up to an image plane, $r_2$ denotes a radius of curvature of a surface on an image side of the first lens, and $r_3$ denotes a radius of curvature of a surface on the object side of the second meniscus lens.

DETAILED DESCRIPTION OF THE INVENTION

Reasons for and effects of adopting such arrangement for an objective optical system for endoscope according to an embodiment of the present invention will be described below by using the accompanying diagrams. However, the present invention is not limited to the embodiment described below.

Figure 1:
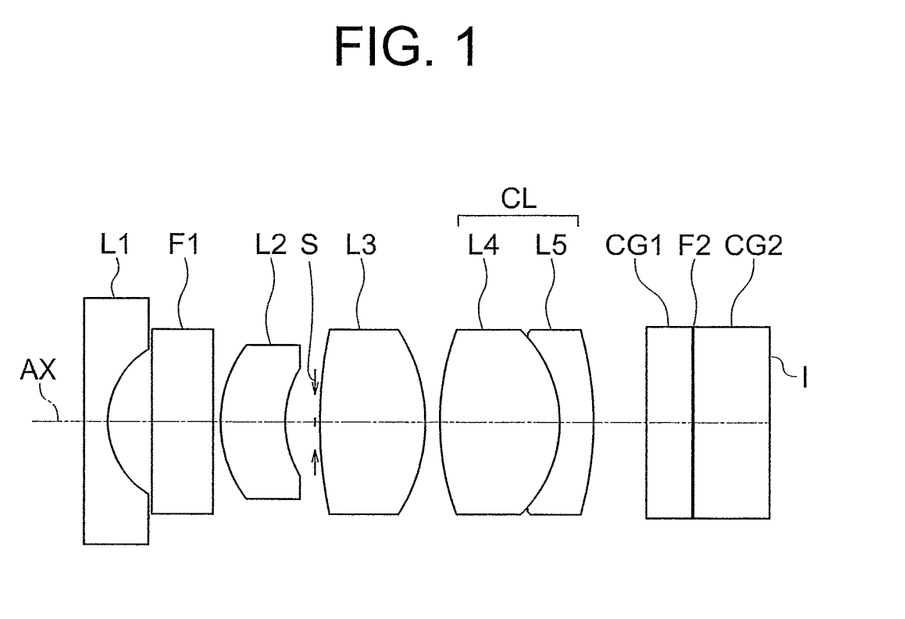
FIG. 1 is a cross-sectional view showing an arrangement of an objective optical system for endoscope according to an embodiment of the present invention.

FIG. 1 is a cross-sectional view showing an arrangement of the objective optical system for endoscope according to the present embodiment.

The objective optical system for endoscope according to the present embodiment is characterized by including in order from an object side, a first lens L1 having a negative refractive power, an infra-red absorbing filter F1, a second meniscus lens L2 having a positive refractive power with a convex surface directed toward the object side, an aperture stop S, a third lens L3 having a biconvex shape, and a cemented lens CL having a positive refractive power as whole, in which a fourth lens L4 having a biconvex shape and a fifth lens L5 having a negative refractive power are cemented, and by satisfying the following conditional expressions (1) and (2).

$$-3 \leq f_1/Ih \leq -1.2 \quad (1)$$

$$0.25 \leq L_{3\_5}/L \leq 0.7 \quad (2)$$

where, $f_1$ denotes a focal length of the first lens L1;

Ih denotes the maximum image height of the objective optical system for endoscope;

$L_{3\_5}$ denotes a distance along an optical axis AX from a surface on the object side of the third lens L3 up to a surface on an image side of the fifth lens L5, and L denotes a distance along the optical axis AX from a surface on the object side of the first lens L1 up to an image plane I.

Firstly, for arranging an objective optical system having a small size and a favorable optical performance which can be used in an endoscope, the first lens L1 having a negative refractive power is disposed nearest to object. Accordingly, it is made possible to adopt an arrangement of a retro-focus type as an arrangement of the objective optical system.

Moreover, the second meniscus lens L2 having a positive refractive power with a convex surface directed toward the object side is disposed. By making such arrangement, an aberration which occurs in the first lens L1 having a negative refractive power is corrected.

The aperture stop S and the third lens L3 having a biconvex shape are disposed on the image side of the second meniscus lens L2. The third lens L3 contributes mainly to image formation. Therefore, a light beam is converged by the positive refractive power of the third lens L3.

At a position where a marginal ray height on the image side of the third lens L3 becomes high, the cemented lens CL in which the fourth lens L4 having a biconvex shape and the fifth lens L5 having a negative refractive power are cemented, is disposed. A chromatic aberration is corrected by the cemented lens CL. The cemented lens CL, in order to contribute to image formation together with the third lens L3 having a positive refractive power, is arranged to have a positive refractive power as a whole.

In such arrangement, for shortening the overall length while letting it to be the retro-focus type arrangement, the first lens L1 having a negative refractive power is required to have a comparatively large negative refractive power. When the negative refractive power of the first lens L1 is let to be excessively large, an amount of aberration such as a spherical aberration and a coma that occur becomes large. Consequently, a favorable optical performance cannot be achieved and a degradation of optical performance due to a manufacturing variability becomes substantial. By setting appropriately the negative refractive power of the first lens L1, an objective optical system with a fast F-number which has both a favorable optical performance and a small-size can be achieved.

For such reason, in the objective optical system for endoscope according to the present embodiment, it is desirable to satisfy the following conditional expression (1).

$$-3 \leq f_1/Ih \leq -1.2 \quad (1)$$

where, $f_1$ denotes a focal length of the first lens L1; and

Ih denotes the maximum image height of the objective optical system for endoscope.

When an upper limit value of conditional expression (1) is exceeded, the negative refractive power becomes excessively large. Accordingly, correction of the spherical aberration and the coma becomes inadequate, and the optical performance is degraded.

When a value falls below a lower limit value of conditional expression (1), the negative refractive power becomes excessively small. Accordingly, the overall length of the objective optical system for endoscope becomes large and small-sizing cannot be carried out.

It is desirable to satisfy the following conditional expression (1') instead of conditional expression (1).

$$-2.5 \leq f_1/Ih \leq -1.25 \quad (1')$$

It is more preferable to satisfy the following conditional expression.

Furthermore, it is more desirable to satisfy the following conditional expression (1'') instead of conditional expression (1).

$$-1.8 \leq f_1/Ih \leq -1.3 \quad (1'')$$

Moreover, for small-sizing of the objective optical system for endoscope, generally, it is desirable to make a lens thickness of each lens and a distance between lenses small. Here, since it is necessary to secure an edge-thickness of a lens, the lens thickness to some extent is necessary.

In the objective optical system for endoscope of the present embodiment, since the F-number is fast, a height of a light ray becomes large. As a result, it becomes difficult to secure an edge thickness of the positive lens. Therefore, for the overall optical length, it is desirable to set the distance between the lenses and the lens thickness of the lenses appropriately. By doing so, it is possible to achieve an objective optical system for endoscope having a fast F-number and a small size.

For such reason, in the objective optical system for endoscope according to the present embodiment, it is desirable to satisfy the following conditional expression (2).

$$0.25 \leq L_{3\_5}/L \leq 0.7 \quad (2)$$

where, $L_{3\_5}$ denotes a distance along an optical axis AX from a surface on the object side of the third lens L3 up to a surface on an image side of the fifth lens L5, and L denotes a distance along the optical axis AX from a surface on the object side of the first lens L1 up to an image plane.

When an upper limit value of conditional expression (2) is exceeded, the overall optical length of the optical system becomes excessively small, and a refractive power of each lens becomes large. Accordingly, a favorable optical performance cannot be achieved.

When a value falls below a lower limit value of conditional expression (2), the optical length becomes excessively large. Consequently, small-sizing of the objective optical system for endoscope becomes difficult, or, the edge thickness of the positive lens becomes excessively small, and a productivity of the lens is degraded.

It is desirable to satisfy the following conditional expression (2') instead of conditional expression (2).

$$0.3 \leq L_{3\_s}/L \leq 0.6 \quad (2')$$

Furthermore, it is more desirable to satisfy the following conditional expression (2") instead of conditional expression (2).

$$0.3 \leq L_{3\_s}/L \leq 0.5 \quad (2")$$

Moreover, for small-sizing the objective optical system for endoscope, it is preferable to make a back focus short. Here, due to manufacturing variability, sometimes, a focusing position is shifted with respect to a designed value. Therefore, for adjusting the focusing position, it is necessary to space lenses at intervals. Moreover, when the second meniscus lens L2 and the third lens L3 sandwiching the aperture stop S are spaced apart, a height of a marginal light ray becomes high, which is effective for aberration correction. Here, when the second meniscus lens L2 and the third lens L3 are spaced apart, small-sizing becomes difficult because of a front-cell diameter becoming large and the overall length of the optical system becoming large.

For such reasons, in the objective optical system for endoscope according to the present embodiment, it is desirable to satisfy the following conditional expressions (3) and (4).

$$0.5 \leq d_{5i}/d_{23} \leq 10 \quad (3)$$

$$3 \leq L/d_{23} \leq 100 \quad (4)$$

where, $d_{5i}$ denotes a distance along the optical axis AX from a surface on the image side of the fifth lens L5 up to the image plane, $d_{23}$ denotes a distance on the optical axis AX from a surface on the image side of the second meniscus lens L2 up to the surface on the object side of the third lens L3, and L denotes a distance along the optical axis AX from the surface on the object side of the first lens L1 up to the image plane.

When upper limit values of conditional expressions (3) and (4) are exceeded, either the overall length of the optical system becomes long, or the distance between the second meniscus lens L2 and the third lens L3 becomes small, thereby making it difficult to reduce an aberration in a peripheral portion of image field.

When values fall below lower limit values of conditional expressions (3) and (4) respectively, either the back focus becomes small and focus adjustment cannot be carried out, or, the distance between the second meniscus lens L2 and the third lens L3 becomes excessively large, and the overall length of the optical system and the front cell become large.

It is desirable to satisfy the following conditional expressions (3') and (4') instead of conditional expressions (3) and (4).

$$0.7 \leq d_{5i}/d_{23} \leq 8.5 \quad (3')$$

$$4 \leq L/d_{23} \leq 60 \quad (4')$$

Furthermore, it is more desirable to satisfy the following conditional expressions (3") and (4") instead of conditional expressions (3) and (4).

$$1 \leq d_{5i}/d_{23} \leq 7 \quad (3")$$

$$5 \leq L/d_{23} \leq 30 \quad (4")$$

Moreover, it is preferable to have the following arrangement for the first lens L1. In an observation by an endoscope, when a dirt or blood is adhered to the lens surface on the object side of the first lens L1, the lens surface is cleaned by jetting water from a nozzle provided to a front end of the endoscope. At the time of cleaning, in a case in which, a shape of the lens surface on the object side of the first lens L1 is a convex shape, the dirt cannot be removed easily. Moreover, in a case in which the lens surface on the object side of the first lens L1 is concave, water removal is not favorable due to accumulation of water. Furthermore, in a case in which the lens surface on the object side of the first lens L1 is concave, it is susceptible to be scratched and cracked due to an impact.

Therefore, the first lens L1 having a negative refractive power is let to be a planoconcave lens and is disposed such that a flat surface is directed toward the object side. By doing so, the water removal during observation is favorable, and cracking of lens due to an impact is reduced.

Moreover, since the second meniscus lens L2 having a positive refractive power corrects an aberration that occurs mainly in the first lens L1, it is preferable to satisfy the following conditional expression (5).

$$7 \leq f_2/Ih \leq 200 \quad (5)$$

where, $f_2$ denotes a focal length of the second meniscus lens L2, and

Ih denotes the maximum image height of the objective optical system for endoscope.

When an upper limit value of conditional expression (5) is exceeded, the refractive power of the second meniscus lens L2 having a positive refractive power becomes excessively small. Accordingly, the coma and a chromatic aberration of magnification occurring in the first lens L1 remains without being corrected adequately.

When a value falls below a lower limit value of conditional expression (5), the refractive power of the second meniscus lens L2 having a positive refractive power becomes excessively large. Accordingly, there is an excessive correction of the coma and the chromatic aberration of magnification, or a concave surface of the first lens L1 becomes excessively deep thereby making the machining of the lens difficult.

It is desirable to satisfy the following conditional expression (5') instead of conditional expression (5).

$$9 \leq f_2/Ih \leq 180 \quad (5')$$

Furthermore, it is more desirable to satisfy the following conditional expression (5") instead of conditional expression (5).

$$11 \leq f_2/Ih \leq 160 \quad (5")$$

Since the aberration in a peripheral portion of image field and the overall length are balanced by the lens arrangement at the front and rear of the aperture stop S, it is preferable to satisfy the following conditional expression (6).

$$-2 \leq f_{12}/f_{345} \leq -0.55 \quad (6)$$

where, $f_{12}$ denotes a combined focal length of lenses from the first lens L1 up to the second meniscus lens L2, and $f_{345}$ denotes a combined focal length of lenses from the third lens L3 up to the fifth lens L5.

When an upper limit value of conditional expression (6) is exceeded, the coma and an astigmatism in the peripheral portion of image field are deteriorated.

When a value falls below a lower limit value of conditional expression (6), since the overall length of the optical system becomes long, the small-sizing becomes difficult.

It is desirable to satisfy the following conditional expression (6') instead of conditional expression (6).

$$-1.6 \leq f_2/f_{345} \leq -0.6 \quad (6')$$

Furthermore, it is more desirable to satisfy the following conditional expression (6") instead of conditional expression (6).

$$-1.2 \leq f_{12}/f_{345} \leq -0.6 \quad (6'')$$

Moreover, for imparting a major imaging effect to the third lens L3 having a positive refractive power, it is preferable that the second meniscus lens L2 having a positive refractive power and the third lens L3 having a positive refractive power satisfy the following conditional expression (7).

$$2 \leq f_2/f_3 \leq 100 \quad (7)$$

where, $f_2$ denotes a focal length of the second meniscus lens L2, and $f_3$ denotes a focal length of the third lens L3.

When an upper limit value of conditional expression (7) is exceeded, either the refractive power of the second meniscus lens L2 having a positive refractive power becomes excessively small, or the refractive power of the third lens L3 having a positive refractive power becomes excessively large. Consequently, the spherical aberration and the coma are deteriorated.

When a value falls below a lower limit value of conditional expression (7), either the refractive power of the second meniscus lens L2 having a positive refractive power becomes excessively large, thereby leading to an excessive correction of the spherical aberration and the coma, or the refractive power of the third lens L3 having a positive refractive power becomes excessively small and the overall length becomes excessively large.

It is desirable to satisfy the following conditional expression (7') instead of conditional expression (7).

$$2.5 \leq f_2/f_3 \leq 85 \quad (7')$$

Furthermore, it is more desirable to satisfy the following conditional expression (7") instead of conditional expression (7).

$$2.5 \leq f_2/f_3 \leq 70 \quad (7'')$$

Moreover, for balancing the small-sizing and the chromatic aberration, it is preferable that the first lens L1 having a negative refractive power and the fifth lens L5 having a negative refractive power, satisfy the following conditional expression (8).

$$0.4 \leq f_1/f_5 \leq 2 \quad (8)$$

where, $f_1$ denotes the focal length of the first lens L1, and $f_5$ denotes a focal length of the fifth lens L5.

When an upper limit value of conditional expression (8) is exceeded, either the refractive power of the first lens L1 having a negative refractive power becomes excessively small and the overall length becomes excessively large, or the refractive power of the fifth lens L5 having a negative refractive power becomes excessively large leading to an excessive correction of the chromatic aberration of magnification and the coma.

When a value falls below a lower limit value of conditional expression (8), either the refractive power of the first lens L1 having a negative refractive power becomes excessively large and the spherical aberration and the coma are deteriorated, or the refractive power of the fifth lens L5 having a negative refractive power becomes excessively small and correction of the chromatic aberration of magnification and the coma is inadequate.

It is desirable to satisfy the following conditional expression (8') instead of conditional expression (8).

$$0.42 \leq f_1/f_5 \leq 1.7 \quad (8')$$

Furthermore, it is more desirable to satisfy the following conditional expression (8") instead of conditional expression (8).

$$0.45 \leq f_1/f_5 \leq 1.5 \quad (8'')$$

Moreover, a substantial aberration occurs at a surface on the image side of the first lens L1 having a negative refractive power. Therefore, it is preferable that a radius of curvature of a surface on an image side of the first lens L1 and a radius of curvature of a surface on the object side of the second meniscus lens L2 satisfy the following conditional expression (9) upon correcting aberration.

$$0.2 \leq r_2/r_3 \leq 0.8 \quad (9)$$

where, $r_2$ denotes a radius of curvature of a surface on an image side of the first lens L1, and $r_3$ denotes a radius of curvature of a surface on the object side of the second meniscus lens L2.

When an upper limit value of conditional expression (9) is exceeded, either the radius of curvature of the first lens L1 having a negative refractive power becomes excessively large and the lens diameter and the overall length become large, or the radius of curvature of the second meniscus lens L2 having a positive refractive power becomes excessively small thereby leading to an excessive correction of the coma and the astigmatism.

When a value falls below a lower limit value of conditional expression (9), either the radius of curvature of the first lens L1 having a negative refractive power becomes excessively small and the spherical aberration and the coma are deteriorated, or the radius of curvature of the second meniscus lens L2 having a positive refractive power becomes excessively large thereby leading to an inadequate correction of the coma and the astigmatism.

It is desirable to satisfy the following conditional expression (9') instead of conditional expression (9).

$$0.3 \leq r_2/r_3 \leq 0.75 \quad (9')$$

Furthermore, it is more desirable to satisfy the following conditional expression (9") instead of conditional expression (9).

$$0.4 \leq r_2/r_3 \leq 0.75 \quad (9'')$$

Moreover, when a lens thickness of the third lens L3 having a positive refractive power which is disposed on the image side of the aperture stop S and a distance between the third lens L3 and the fourth lens L4 having a positive refractive power are made large, the height of a marginal light ray becomes large. Consequently, it is effective for an aberration correction in the peripheral portion of image field. However, the overall optical length becomes large.

For this reason, for balancing the favorable correction of aberration in the peripheral portion of image field and the overall length of the optical system, it is preferable to satisfy the following conditional expression (10).

$$2 \leq d_3/d_{34} \leq 15 \quad (10)$$

where, $d_3$ denotes a lens thickness of the third lens L3, and $d_{34}$ denotes a distance along the optical axis from a surface on an image side of the third lens L3 up to a surface on an object side of the fourth lens L4.

When an upper limit value of conditional expression (10) is exceeded, either the lens thickness of the third lens L3 having a positive refractive power becomes excessively large and the overall length becomes long, or the distance of the fourth lens L4 having a positive refractive power becomes excessively small and the coma and the astigmatism are deteriorated.

When a value falls below a lower limit value of conditional expression (10), either the lens thickness of the third lens L3 having a positive refractive power becomes excessively thin and lens workability is deteriorated leading to a rise in cost, or the distance of the fourth lens L4 having a positive refractive power becomes excessively large and the lens diameter and the overall length become large.

It is desirable to satisfy the following conditional expression (10') instead of conditional expression (10).

$$3.5 \leq d_3/d_{34} \leq 12 \tag{10'}$$

Furthermore, it is more desirable to satisfy the following conditional expression (10") instead of conditional expression (10).

$$5 \leq d_3/d_{34} \leq 10 \tag{10''}$$

Moreover, it is desirable that the objective optical system for endoscope of the present embodiment satisfies the following conditional expression (11).

$$2 \leq Fno \leq 4.5 \tag{11}$$

where,

Fno denotes an F-number for the objective optical system for endoscope.

When an upper limit value of conditional expression (11) is exceeded, there is an effect of diffraction on the pixel pitch of the image pickup element, and favorable optical performance cannot be achieved.

When a value falls below a lower limit value of conditional expression (11), the aberration that remains becomes excessively large, and a favorable optical performance cannot be achieved.

It is desirable to satisfy the following conditional expression (11') instead of conditional expression (11).

$$2.5 \leq Fno \leq 4.2 \tag{11'}$$

Furthermore, it is more desirable to satisfy the following conditional expression (11") instead of conditional expression (11).

$$2.8 \leq Fno \leq 3.8 \tag{11''}$$

EXAMPLE 1

An objective optical system for endoscope according to an example 1 of the present invention will be described below.

Figure 2A:
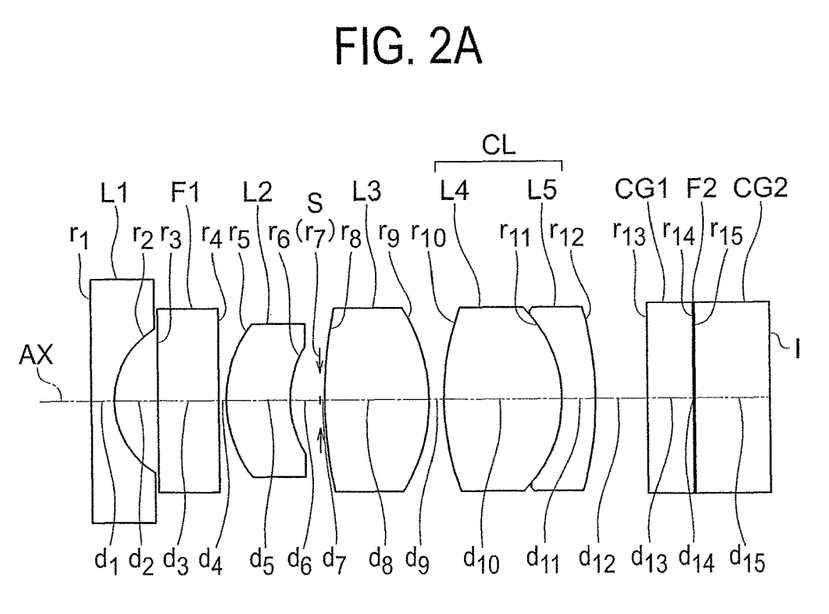
FIG. 2A is a cross-sectional view showing an arrangement of an objective optical system for endoscope according to an example 1 of the present invention.
Figure 2B:
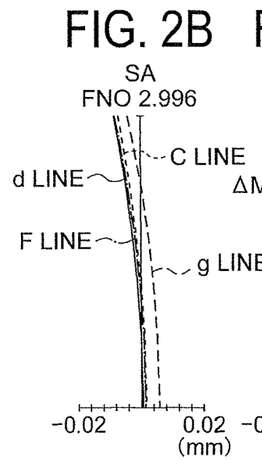
FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively.
Figure 2C:
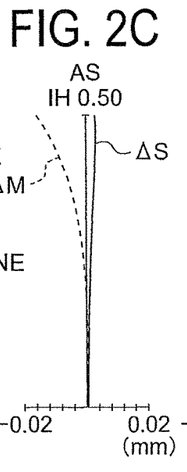
Figure 2D:
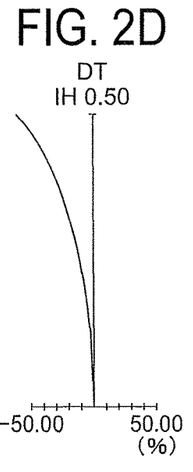
Figure 2E:
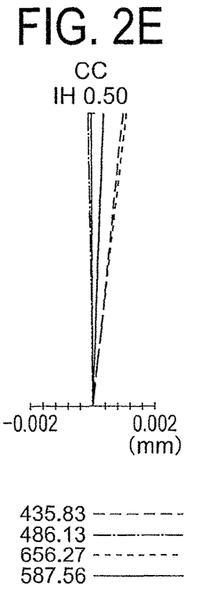

FIG. 2A is a cross-sectional view of the objective optical system for endoscope according to the present example, FIG. 2B shows a spherical aberration (SA), FIG. 2C shows an astigmatism (AS), FIG. 2D shows a distortion (DT), and FIG. 2E shows a chromatic aberration of magnification (CC).

The objective optical system for endoscope according to the present example includes in order from an object side, a first lens L1 having a negative refractive power and a planoconcave shape with a flat surface directed toward the object side, an infra-red absorbing filter F1, a second meniscus lens L2 having a positive refractive power with a convex surface thereof directed toward the object side, an aperture stop S, a third lens L3 having a positive refractive power and a biconvex shape, a fourth lens L4 having a positive refractive power and a biconvex shape, a fifth meniscus lens L5 having a negative refractive power with a convex surface thereof directed toward an image side, a cover glass CG1, and a CCD cover glass CG2. Here, the fourth lens L4 having a positive refractive power and the fifth meniscus lens L5 having a negative refractive power are cemented. The cover glass CG1 and the CCD cover glass CG2 are cemented via a cemented layer F2. Moreover, a YAG (yttrium aluminum garnet) laser cut coating is applied to an object side of the infra-red absorbing filter F1 and an LD laser cut coating is applied to an image side of the infra-red absorbing filter F1. Moreover, in all the examples that follow, I denotes an image pickup surface.

EXAMPLE 2

An objective optical system for endoscope according to an example 2 of the present invention will be described below.

Figure 3A:
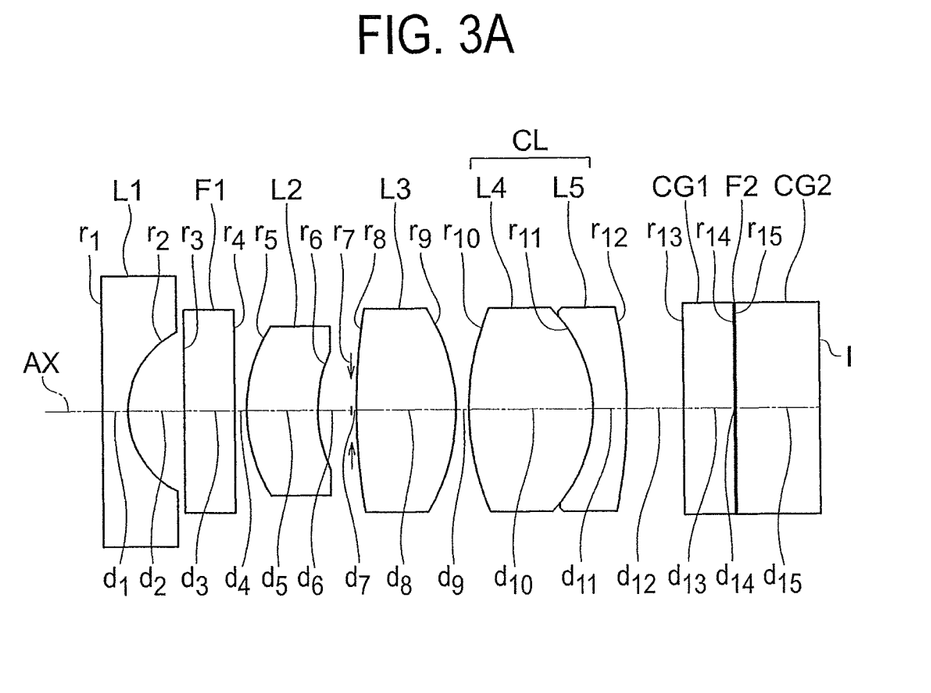
FIG. 3A is a cross-sectional view showing an arrangement of an objective optical system for endoscope according to an example 2 of the present invention.
Figure 3B:
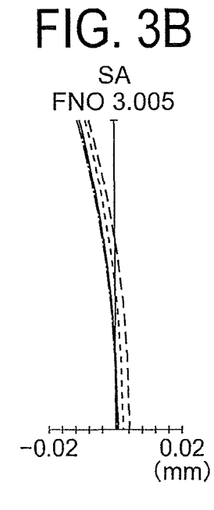
FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively.
Figure 3C:
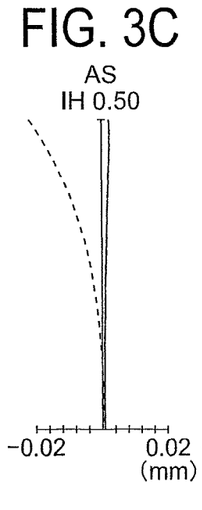
Figure 3D:
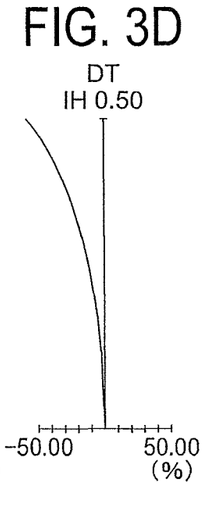
Figure 3E:
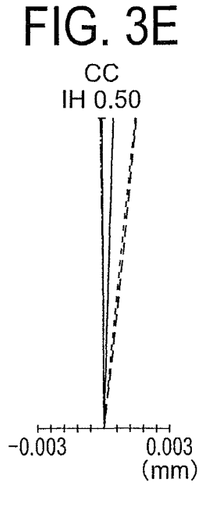

FIG. 3A is a cross-sectional view of the objective optical system for endoscope according to the present example, FIG. 3B shows a spherical aberration (SA), FIG. 3C shows an astigmatism (AS), FIG. 3D shows a distortion (DT), and FIG. 3E shows a chromatic aberration of magnification (CC).

The objective optical system for endoscope according to the present example includes in order from an object side, a first lens L1 having a negative refractive power and a planoconcave shape with a flat surface directed toward the object side, an infra-red absorbing filter F1, a second meniscus lens L2 having a positive refractive power with a convex surface thereof directed toward the object side, an aperture stop S, a third lens L3 having a positive refractive power and a biconvex shape, a fourth lens L4 having a positive refractive power and a biconvex shape, a fifth meniscus lens L5 having a negative refractive power with a convex surface thereof directed toward an image side, a cover glass CG1, and a CCD cover glass CG2. Here, the fourth lens L4 having a positive refractive power and the fifth meniscus lens L5 having a negative refractive power are cemented. The cover glass CG1 and the CCD cover glass CG2 are cemented via a cemented layer F2. Moreover, a YAG laser cut coating is applied to an object side of the infra-red absorbing filter F1 and an LD laser cut coating is applied to an image side of the infra-red absorbing filter F1.

EXAMPLE 3

An objective optical system for endoscope according to an example 3 of the present invention will be described below.

Figure 4A:
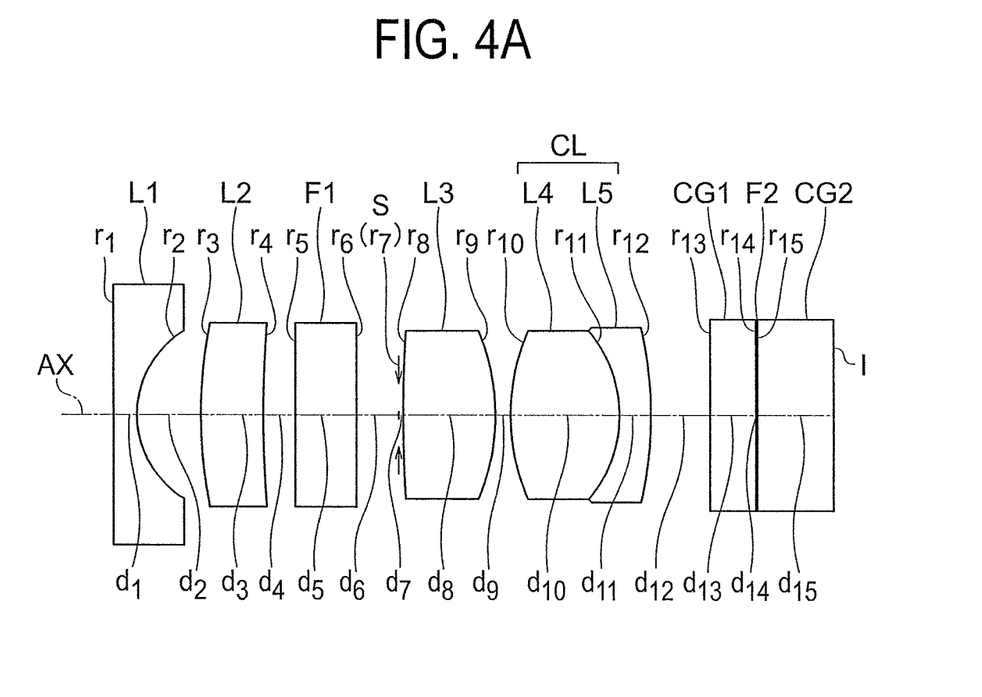
FIG. 4A is a cross-sectional view showing an arrangement of an objective optical system for endoscope according to an example 3 of the present invention.
Figure 4B:
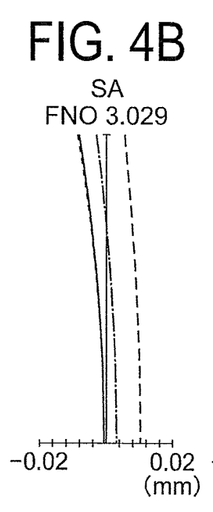
FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively.
Figure 4C:
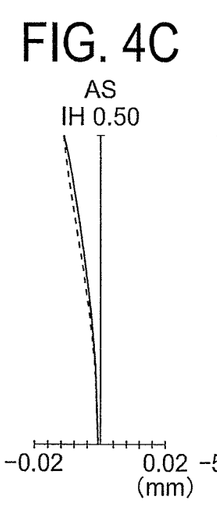
Figure 4D:
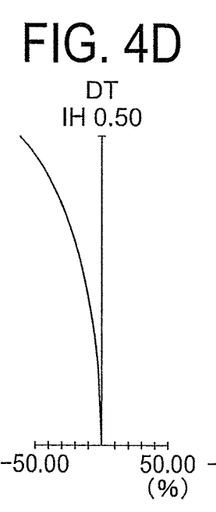
Figure 4E:
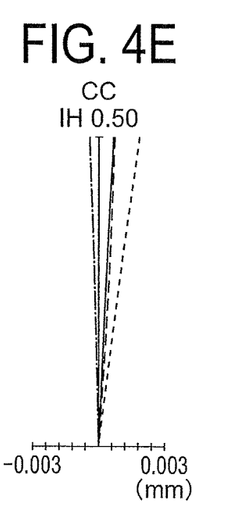

FIG. 4A is a cross-sectional view of the objective optical system for endoscope according to the present example, FIG. 4B shows a spherical aberration (SA), FIG. 4C shows an astigmatism, FIG. 4D shows a distortion (DT), and FIG. 4E shows a chromatic aberration of magnification (CC).

The objective optical system for endoscope according to the present example includes in order from an object side, a first lens L1 having a negative refractive power and a planoconcave shape with a flat surface directed toward the object side, a second meniscus lens L2 having a positive refractive power with a convex surface thereof directed toward the object side, an infra-red absorbing filter F1, an aperture stop S, a third lens L3 having a positive refractive power and a biconvex shape, a fourth lens L4 having a positive refractive power and a biconvex shape, a fifth meniscus lens L5 having a negative refractive power with a convex surface thereof directed toward an image side, a cover glass CG1, and a CCD cover glass CG2. Here, the fourth lens L4 having a positive refractive power and the fifth meniscus lens L5 having a negative refractive power are cemented. The cover glass CG1 and the CCD cover glass CG2 are cemented via a cemented layer F2. Moreover, a YAG laser cut coating is applied to an object side of the infra-red absorbing filter F1 and an LD laser cut coating is applied to an image side of the infra-red absorbing filter F1.

EXAMPLE 4

An objective optical system for endoscope according to an example 4 of the present invention will be described below.

Figure 5A:
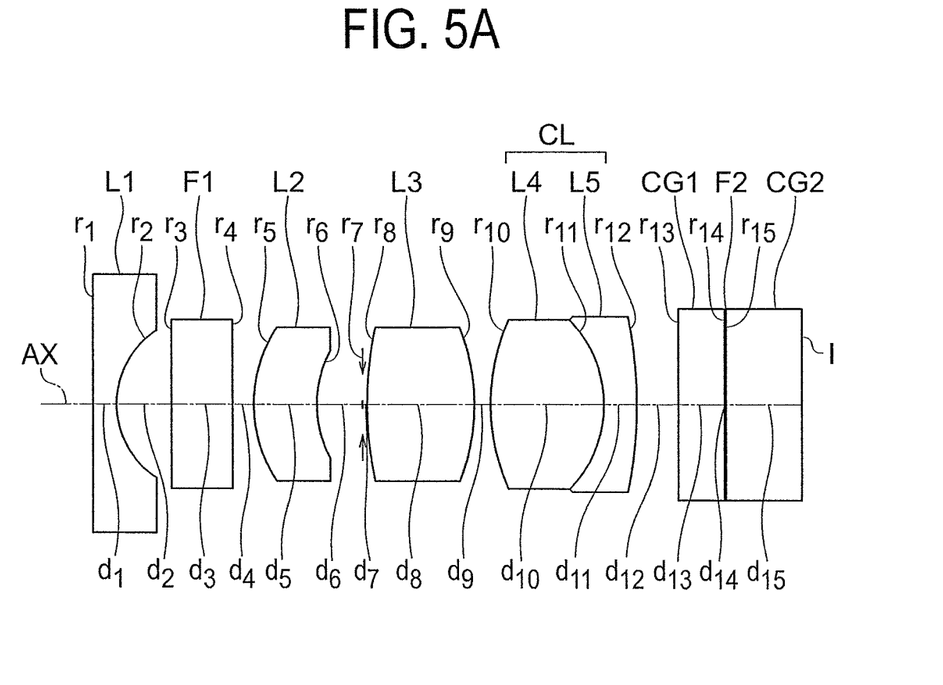
FIG. 5A is a cross-sectional view showing an arrangement of an objective optical system for endoscope according to an example 4 of the present invention.
Figure 5B:
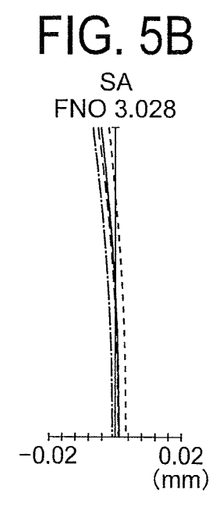
FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively.
Figure 5C:
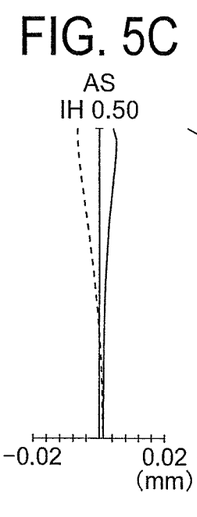
Figure 5D:
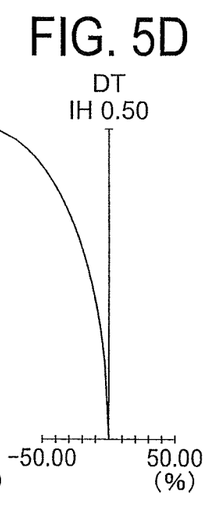
Figure 5E:
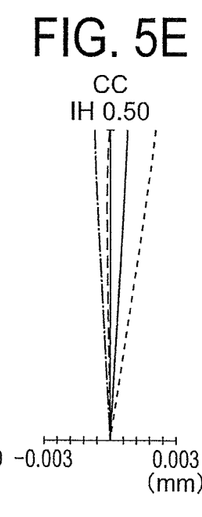

FIG. 5A is a cross-sectional view of the objective optical system for endoscope according to the present example, FIG. 5E shows a spherical aberration (SA), FIG. 5C shows an astigmatism (AS), FIG. 5D shows a distortion (DT), and FIG. 5E shows a chromatic aberration of magnification (CC).

The objective optical system for endoscope according to the present example includes in order from an object side, a first lens L1 having a negative refractive power and a planoconcave shape with a flat surface directed toward the object side, an infra-red absorbing filter F1, a second meniscus lens L2 having a positive refractive power with a convex surface directed toward the object side, an aperture stop S, a third lens L3 having a positive refractive power and a biconvex shape, a fourth lens L4 having a positive refractive power and a biconvex shape, a fifth meniscus lens L5 having a negative refractive power with a convex surface thereof directed toward an image side, a cover glass CG1, and a CCD cover glass CG2. Here, the fourth lens L4 having a positive refractive power and a fifth meniscus lens L5 having a negative refractive power are cemented. The cover glass CG1 and the CCD cover glass CG2 are cemented via a cemented layer F2. Moreover, a YAG laser cut coating is applied to an object side of the infra-red absorbing filter F1 and an LD laser cut coating is applied to an image side of the infra-red absorbing filter F1.

EXAMPLE 5

An objective optical system for endoscope according to an example 5 of the present invention will be described below.

Figure 6A:
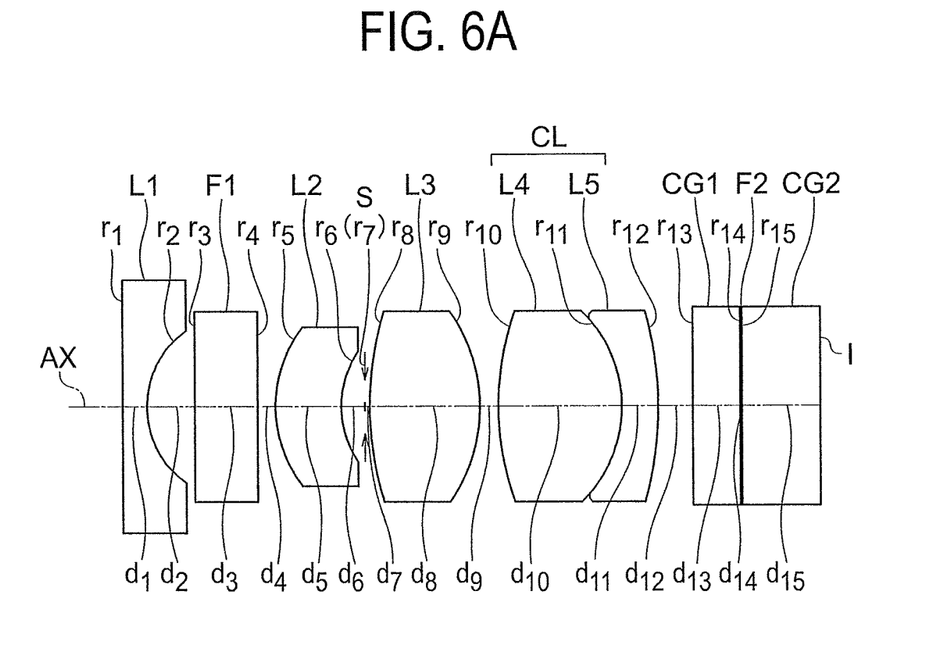
FIG. 6A is a cross-sectional view showing an arrangement of an objective optical system for endoscope according to an example 5 of the present invention.
Figure 6B:
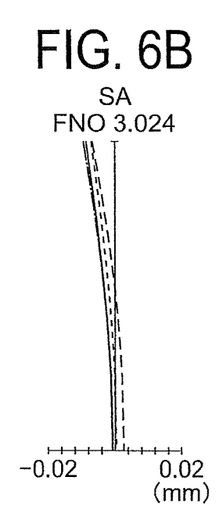
FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively.
Figure 6C:
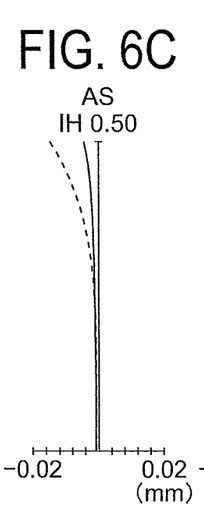
Figure 6D:
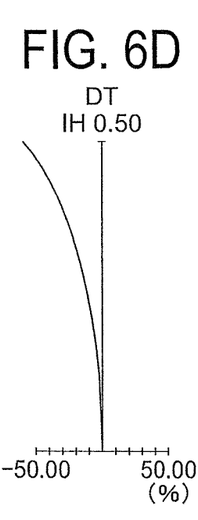
Figure 6E:
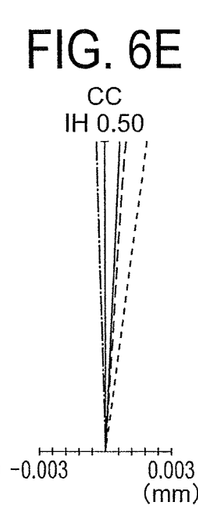

FIG. 6A is a cross-sectional view of the objective optical system for endoscope according to the present example, FIG. 6B shows a spherical aberration (SA), FIG. 6O shows an astigmatism (AS), FIG. 6D shows a distortion (DT), and FIG. 6E shows a chromatic aberration of magnification (CC).

The objective optical system for endoscope according to the present example includes in order from an object side, a first lens L1 having a negative refractive power and a planoconcave shape with a flat surface directed toward the object side, an infra-red absorbing filter F1, a second meniscus lens L2 having a positive refractive power with a convex surface directed toward the object side, an aperture stop S, a third lens L3 having a positive refractive power and a biconvex shape, a fourth lens L4 having a positive refractive power and a biconvex shape, a fifth meniscus lens L5 having a negative refractive power with a convex surface thereof directed toward an image side, a cover glass CG1, and a CCD cover glass CG2. Here, the fourth lens L4 having a positive refractive power and a fifth meniscus lens L5 having a negative refractive power are cemented. The cover glass CG1 and the CCD cover glass CG2 are cemented via a cemented layer F2. Moreover, a YAG laser cut coating is applied to an object side of the infra-red absorbing filter F1 and an LD laser cut coating is applied to an image side of the infra-red absorbing filter F1.

Numerical data for each example is shown below. Regarding symbols, r denotes a radius of curvature of each lens surface, d denotes a distance between two lens surfaces, ne denotes a refractive index for an e-line, vd denotes Abbe's number for each lens, Fno denotes an F-number, ω denotes a half angle of view, and IH denotes an image height.

EXAMPLE 1

| Unit mm | | | | |
|---|---|---|---|---|
| Surface data | | | | |
| Surface no. | r | d | ne | vd |
| 1 | ∞ | 0.167 | 1.88815 | 40.76 |
| 2 | 0.6099 | 0.3197 | | |
| 3 | ∞ | 0.4454 | 1.515 | 75.00 |
| 4 | ∞ | 0.0538 | | |
| 5 | 0.918 | 0.465 | 1.97189 | 17.47 |
| 6 | 0.7442 | 0.2227 | | |
| 7(Stop) | ∞ | 0.0334 | | |
| 8 | 3.1089 | 0.7745 | 1.77621 | 49.60 |
| 9 | −1.2282 | 0.1044 | | |
| 10 | 1.9026 | 0.8651 | 1.73234 | 54.68 |
| 11 | −0.9327 | 0.2487 | 1.97189 | 17.47 |
| 12 | −2.4013 | 0.3813 | | |
| 13 | ∞ | 0.3341 | 1.51825 | 64.14 |
| 14 | ∞ | 0.01 | 1.515 | 64.00 |
| 15 | ∞ | 0.5568 | 1.507 | 63.26 |
| 16(Image pickup surface) | ∞ | | | |

| Various data | |
|---|---|
| Fno. | 3.015 |
| ω | 67.5° |
| IH | 0.5 mm |

EXAMPLE 2

| Unit mm | | | | |
|---|---|---|---|---|
| Surface data | | | | |
| Surface no. | r | d | ne | vd |
| 1 | ∞ | 0.167 | 1.88815 | 40.76 |
| 2 | 0.5845 | 0.3708 | | |
| 3 | ∞ | 0.3341 | 1.515 | 75.00 |
| 4 | ∞ | 0.0775 | | |
| 5 | 1.061 | 0.465 | 1.97189 | 17.47 |
| 6 | 0.9481 | 0.2227 | | |
| 7(Stop) | ∞ | 0.0334 | | |
| 8 | 4.0859 | 0.66 | 1.82017 | 46.62 |
| 9 | −1.2835 | 0.084 | | |
| 10 | 1.6799 | 0.8172 | 1.73234 | 54.68 |
| 11 | −0.9589 | 0.2225 | 1.97189 | 17.47 |
| 12 | −3.2598 | 0.3712 | | |

-continued

| Unit mm | | | | |
|---|---|---|---|---|
| 13 | ∞ | 0.3341 | 1.51825 | 64.14 |
| 14 | ∞ | 0.01 | 1.515 | 64.00 |
| 15 | ∞ | 0.5568 | 1.507 | 63.26 |
| 16(Image pickup surface) | ∞ | | | |

| Various data | |
|---|---|
| Fno. | 3.032 |
| ω | 66.1° |
| IH | 0.5 mm |

EXAMPLE 3

| Unit mm | | | | |
|---|---|---|---|---|
| Surface data | | | | |
| Surface no. | r | d | ne | νd |
| 1 | ∞ | 0.167 | 1.88815 | 40.76 |
| 2 | 0.7213 | 0.4616 | | |
| 3 | 3.4184 | 0.4541 | 1.97189 | 17.47 |
| 4 | 8.6746 | 0.2307 | | |
| 5 | ∞ | 0.4454 | 1.515 | 75.00 |
| 6 | ∞ | 0.314 | | |
| 7(Stop) | ∞ | 0.0334 | | |
| 8 | 9.8099 | 0.6679 | 1.73234 | 54.68 |
| 9 | −1.6116 | 0.1114 | | |
| 10 | 1.5616 | 0.7869 | 1.69979 | 55.53 |
| 11 | −0.9511 | 0.2298 | 1.97189 | 17.47 |
| 12 | −2.8924 | 0.4302 | | |
| 13 | ∞ | 0.3341 | 1.51825 | 64.14 |
| 14 | ∞ | 0.01 | 1.515 | 64.00 |
| 15 | ∞ | 0.5568 | 1.507 | 63.26 |
| 16(Image pickup surface) | ∞ | | | |

| Various data | |
|---|---|
| Fno. | 3.054 |
| ω | 68.1° |
| IH | 0.5 mm |

EXAMPLE 4

| Unit mm | | | | |
|---|---|---|---|---|
| Surface data | | | | |
| Surface no. | r | d | ne | νd |
| 1 | ∞ | 0.167 | 1.88815 | 40.76 |
| 2 | 0.6351 | 0.4002 | | |
| 3 | ∞ | 0.4454 | 1.515 | 75.00 |
| 4 | ∞ | 0.1518 | | |
| 5 | 1.0084 | 0.4561 | 1.93429 | 18.90 |
| 6 | 0.8149 | 0.3361 | | |
| 7(Stop) | ∞ | 0.0334 | | |
| 8 | 2.5467 | 0.7796 | 1.82017 | 46.62 |
| 9 | −1.5164 | 0.1172 | | |
| 10 | 1.4843 | 0.8253 | 1.65425 | 58.55 |
| 11 | −0.8704 | 0.2371 | 1.93429 | 18.90 |
| 12 | −3.2278 | 0.3005 | | |
| 13 | ∞ | 0.3341 | 1.51825 | 64.14 |
| 14 | ∞ | 0.01 | 1.515 | 64.00 |

-continued

| Unit mm | | | | |
|---|---|---|---|---|
| 15 | ∞ | 0.5568 | 1.507 | 63.26 |
| 16(Image pickup surface) | ∞ | | | |

| Various data | |
|---|---|
| Fno. | 3.051 |
| ω | 81.4° |
| IH | 0.5 mm |

EXAMPLE 5

| Unit mm | | | | |
|---|---|---|---|---|
| Surface data | | | | |
| Surface no. | r | d | ne | νd |
| 1 | ∞ | 0.167 | 1.88815 | 40.76 |
| 2 | 0.6531 | 0.3373 | | |
| 3 | ∞ | 0.4454 | 1.515 | 75.00 |
| 4 | ∞ | 0.1247 | | |
| 5 | 0.906 | 0.465 | 1.97189 | 17.47 |
| 6 | 0.6853 | 0.1703 | | |
| 7(Stop) | ∞ | 0.0334 | | |
| 8 | 2.1631 | 0.7787 | 1.77621 | 49.60 |
| 9 | −1.1703 | 0.1299 | | |
| 10 | 1.9727 | 0.8736 | 1.73234 | 54.68 |
| 11 | −0.923 | 0.2548 | 1.97189 | 17.47 |
| 12 | −2.4452 | 0.2455 | | |
| 13 | ∞ | 0.3341 | 1.51825 | 64.14 |
| 14 | ∞ | 0.01 | 1.515 | 64.00 |
| 15 | ∞ | 0.5568 | 1.507 | 63.26 |
| 16(Image pickup surface) | ∞ | | | |

| Various data | |
|---|---|
| Fno. | 3.043 |
| ω | 67.0° |
| IH | 0.5 mm |

Values of the conditional expressions (1)-(11) in the objective optical System for endoscope according to examples 1-5.
Conditional Expression

| | Example1 | Example2 | Example3 | Example4 | Example5 |
|---|---|---|---|---|---|
| (1) $f_1/Ih$ | −1.37 | −1.32 | −1.62 | −1.43 | −1.47 |
| (2) $L_{3\_5}/L$ | 0.40 | 0.38 | 0.34 | 0.38 | 0.41 |
| (3) $d_{5}/d_{23}$ | 5.0 | 5.0 | 1.3 | 3.3 | 5.6 |
| (4) $L/d_{23}$ | 19.5 | 18.5 | 5.1 | 13.9 | 24.2 |
| (5) $f_2/Ih$ | 25.4 | 17.8 | 11.1 | 65.8 | 150.4 |
| (6) $f_{12}/f_{345}$ | −0.63 | −0.69 | −0.94 | −0.63 | −0.64 |
| (7) $f_2/f_3$ | 10.3 | 7.1 | 2.9 | 25.9 | 69.0 |
| (8) $f_1/f_5$ | 0.40 | 0.45 | 0.53 | 0.53 | 0.44 |
| (9) $r_2/r_3$ | 0.66 | 0.55 | 0.21 | 0.63 | 0.72 |
| (10) $d_3/d_{34}$ | 7.4 | 7.9 | 6.0 | 6.7 | 6.0 |
| (11) Fno | 3.02 | 3.03 | 3.05 | 3.05 | 3.04 |

As described above, the present invention is useful for an objective optical system for endoscope which is small-sized, and has a favorable optical performance and a fast F-number.

An objective optical system for endoscope according to an embodiment of the present invention shows an effect of having a small size, a favorable optical performance, and a fast F-number such as about 3.

What is claimed is:

1. An objective optical system for endoscope, comprising in order from an object side:
   a first lens having a negative refractive power;
   a second meniscus lens having a positive refractive power with a convex surface thereof directed toward the object side;
   an aperture stop;
   a third lens having a biconvex shape, and
   a cemented lens having a positive refractive power as a whole, in which a fourth lens having a biconvex shape and a fifth lens having a negative refractive power are cemented, wherein
   the objective optical system for endoscope satisfies the following conditional expressions (1), (2), and (9)

$$-3 \leq f_1/Ih \leq -1.2 \tag{1}$$

$$0.25 \leq L_{3\_5}/L \leq 0.7 \tag{2}$$

$$0.2 \leq r_2/r_3 \leq 0.8 \tag{9}$$

where,
   $f_1$ denotes a focal length of the first lens;
   $Ih$ denotes the maximum image height of the objective optical system for endoscope;
   $L_{3\_5}$ denotes a distance along an optical axis from a surface on the object side of the third lens up to a surface on an image side of the fifth lens,
   $L$ denotes a distance along the optical axis from a surface on the object side of the first lens up to an image plane,
   $r_2$ denotes a radius of curvature of a surface on an image side of the first lens, and
   $r_3$ denotes a radius of curvature of a surface on the object side of the second meniscus lens.

2. The objective optical system for endoscope according to claim 1, wherein the objective optical system for endoscope satisfies the following conditional expressions (3) and (4)

$$0.5 \leq d_{5i}/d_{23} \leq 10 \tag{3}$$

$$3 \leq L/d_{23} \leq 100 \tag{4}$$

where,
   $d_{5i}$ denotes a distance along the optical axis from a surface on the image side of the fifth lens up to the image plane,
   $d_{23}$ denotes a distance on the optical axis from a surface on the image side of the second meniscus lens up to the surface on the object side of the third lens, and
   $L$ denotes a distance along the optical axis from the surface on the object side of the first lens up to the image plane.

3. The objective optical system for endoscope according to claim 1, wherein the first lens has a planoconcave shape with a flat surface directed toward the object side.

4. The objective optical system for endoscope according to claim 1, wherein the objective optical system for endoscope satisfies the following conditional expression (5)

$$7 \leq f_2/Ih \leq 200 \tag{5}$$

where,
   $f_2$ denotes a focal length of the second meniscus lens, and
   $Ih$ denotes the maximum image height of the objective optical system for endoscope.

5. The objective optical system for endoscope according to claim 1, wherein the objective optical system for endoscope satisfies the following conditional expression (6)

$$-2 \leq f_{12}/f_{345} \leq -0.55 \tag{6}$$

where,
   $f_{12}$ denotes a combined focal length of lenses from the first lens up to the second meniscus lens, and
   $f_{345}$ denotes a combined focal length of lenses from the third lens up to the fifth lens.

6. The objective optical system for endoscope according to claim 1, wherein the objective optical system for endoscope satisfies the following conditional expression (7)

$$2 \leq f_2/f_3 \leq 100 \tag{7}$$

where,
   $f_2$ denotes a focal length of the second meniscus lens, and
   $f_3$ denotes a focal length of the third lens.

7. The objective optical system for endoscope according to claim 1, wherein the objective optical system for endoscope satisfies the following conditional expression (8)

$$0.4 \leq f_1/f_5 \leq 2 \tag{8}$$

where,
   $f_1$ denotes the focal length of the first lens, and
   $f_5$ denotes a focal length of the fifth lens.

8. The objective optical system for endoscope according to claim 1, wherein the objective optical system for endoscope satisfies the following conditional expression (10)

$$2 \leq d_3/d_{34} \leq 15 \tag{10}$$

where,
   $d_3$ denotes a lens thickness of the third lens, and
   $d_{34}$ denotes a distance along the optical axis from a surface on an image side of the third lens up to a surface on an object side of the fourth lens.

* * * * *